(12) United States Patent
Van Aert et al.

(10) Patent No.: US 12,359,080 B2
(45) Date of Patent: *Jul. 15, 2025

(54) AQUEOUS DISPERSION OF CAPSULES

(71) Applicant: AGFA-GEVAERT NV, Mortsel (BE)

(72) Inventors: Hubertus Van Aert, Mortsel (BE); Johan Loccufier, Mortsel (BE); Jos Louwet, Mortsel (BE)

(73) Assignee: Agfa-Gevaert NV, Mortsel (BE)

( * ) Notice: Subject to any disclaimer, the term of this patent is extended or adjusted under 35 U.S.C. 154(b) by 1078 days.

This patent is subject to a terminal disclaimer.

(21) Appl. No.: 17/298,687

(22) PCT Filed: Nov. 26, 2019

(86) PCT No.: PCT/EP2019/082632
§ 371 (c)(1),
(2) Date: Jun. 1, 2021

(87) PCT Pub. No.: WO2020/114839
PCT Pub. Date: Jun. 11, 2020

(65) Prior Publication Data
US 2022/0041878 A1   Feb. 10, 2022

(30) Foreign Application Priority Data

Dec. 3, 2018  (EP) ..................... 18209746

(51) Int. Cl.
*C09D 11/328*  (2014.01)
*A01N 25/04*  (2006.01)
(Continued)

(52) U.S. Cl.
CPC ............ *C09D 11/328* (2013.01); *A01N 25/04* (2013.01); *A01P 15/00* (2021.08); *B01J 13/16* (2013.01);
(Continued)

(58) Field of Classification Search
CPC ... C09D 11/328; C09D 11/033; C09D 11/037; C09D 11/102; C09D 11/322;
(Continued)

(56) References Cited

U.S. PATENT DOCUMENTS 5,635,211 A  6/1997 Nehen et al.
6,586,107 B2  7/2003 Klug et al.
(Continued)

FOREIGN PATENT DOCUMENTS

EP  2933374 A1  10/2015
EP  3095825 A1  11/2016
(Continued)

OTHER PUBLICATIONS

Guerre, M. Fluorinated Vitrimer Elastomers with a Dual Temperature Response Journal of the American Chemical Society 2018, 140 (41), 13272-13284 (Year: 2018).*
(Continued)

*Primary Examiner* — Andrew J. Oyer
*Assistant Examiner* — Cullen L G Davidson
(74) *Attorney, Agent, or Firm* — Leydig, Voit & Mayer, Ltd.

(57) ABSTRACT

An aqueous dispersion of particles comprising a resin having at least one repeating unit of formula I, II and/or III and which is obtainable by contacting in a liquid comprising water, a compound A comprising at least 2 functional groups selected from the group of functional groups —X—C(=O)—CHR1-C(=O)—R2, —X—C(=O)—C≡C—R2; or —X—C(=O)—CR1=CR2-NR11R12, the functional groups are linked by a linking group comprising a polyester, polyether, polyolefin, polydimethylsiloxane or polycarbonate chain with a compound B comprising at least two —NH$_2$, —NH$_3^+$ or —N=C=O, wherein X, R1, R2, R3, R11 and R12 have the same meaning as that defined in the claims and w. The invention also includes a method of producing the aqueous dispersion.

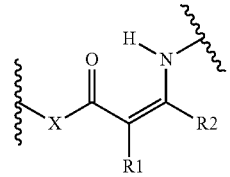

(I)

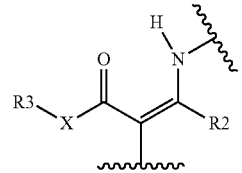

(II)

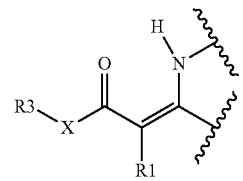

(III)

16 Claims, No Drawings

(51) Int. Cl.
*A01P 15/00* (2006.01)
*B01J 13/16* (2006.01)
*B41M 5/00* (2006.01)
*C09D 11/033* (2014.01)
*C09D 11/037* (2014.01)
*C09D 11/102* (2014.01)
*C09D 11/322* (2014.01)

(52) U.S. Cl.
CPC ......... *B41M 5/0023* (2013.01); *C09D 11/033* (2013.01); *C09D 11/037* (2013.01); *C09D 11/102* (2013.01); *C09D 11/322* (2013.01)

(58) Field of Classification Search
CPC ......... A01N 25/04; A01N 25/28; A01P 15/00; B01J 13/16; B41M 5/0023; C09B 67/0097; C11D 3/505; C11D 17/0039; A61K 9/5021; A61K 9/513
See application file for complete search history.

(56) References Cited

U.S. PATENT DOCUMENTS

| | | |
|---|---|---|
| 6,797,670 B2 | 9/2004 | Kleban et al. |
| 11,214,700 B2 * | 1/2022 | Desmet .................. C08G 12/00 |
| 2011/0077188 A1 | 3/2011 | Quali et al. |

FOREIGN PATENT DOCUMENTS

| | | |
|---|---|---|
| EP | 3441223 A1 | 2/2019 |
| WO | 2011/154893 A1 | 12/2011 |
| WO | 2012/107323 A1 | 8/2012 |
| WO | 2015/158649 A1 | 10/2015 |
| WO | 2016/097169 A1 | 6/2016 |

OTHER PUBLICATIONS

International Search Report dated Jan. 28, 2020 relating to PCT/EP2019/082632, 5 pages.

Written Opinion dated Jan. 28, 2020 relating to PCT/EP2019/082632, 5 pages.

Zhang, Yufen et al., Characterisation and applications of microcapsules obtained by interfacial polycondensation, Journal of Microencapsulation, (2012) 29(7), pp. 636-649.

Salaun, Fabien, Microencapsulation by Interfacial Polymerization, Chapter 5, Encapsulation Nanotechnologies (2013) pp. 137-173.

* cited by examiner

AQUEOUS DISPERSION OF CAPSULES

REFERENCE TO RELATED APPLICATIONS

This application is a 371 National Stage Application of PCT/EP2019/082632, filed Nov. 26, 2019, which claims the benefit of European Application No. 18209746.9, filed Dec. 3, 2018, the contents of which are incorporated by reference herein in their entirety.

TECHNICAL FIELD

The present invention relates to aqueous dispersions of nano- or microcapsules. The core may contain an active material. The dispersion can be used in aqueous formulations such as aqueous based paints, inks, inkjet inks, drugs, perfumes, etc.

BACKGROUND ART

Nano- or micro-encapsulation is used in a variety of different applications where there is a need to deliver, apply, or release an active material including a fragrance, a flavour or malodour counteraction agent, a flame-retardant, a drug, a herbicide, a pesticide to a target area in a time-delayed or controlled manner.

Various techniques for preparing capsules are known in the art and are used, depending on the contents to be encapsulated, the environment in which the capsules should retain their integrity and the desired release mechanism.

Interfacial polycondensation is a known technique for preparing capsules and versatile capsule wall materials are used including polyureas and polyurethanes (WO 2011/154893, WO 2012/107323, US 2011/0077188, U.S. Pat. Nos. 5,635,211, 6,586,107, and 6,797,670). Such wall materials are produced by having a first phase which is water immiscible and includes a polyfunctional isocyanate and a second aqueous phase which includes (i) a polyfunctional alcohol (i.e., a polyol) having two or more —OH groups for obtaining a polyurethane capsule wall, or (ii) a polyfunctional amine (i.e., a polyamine) having two or more —NH2 and/or —NH groups for obtaining a polyurea capsule wall.

Known polyurea or polyurethane capsules face various issues, e.g., low stability, low solvent resistance, high toxicity, high wall permeability, absence of temperature controlled delivery of the active material in the core and requiring toxic and dangerous isocyanate compounds during the production.

There is a need to develop safe, stable, and high efficient capsules for use in laundry, washing, cleaning, surface care and personal and skin care, drug delivery, printing, textile printing and treatment. For such applications, quicker and easier release are often desirable. Also, it would be desirable to more precisely influence the capsule wall permeability, resistance to solvents and other capsule wall properties to achieve the desired release profile and consumer benefits.

SUMMARY OF INVENTION

It is the objective of the present invention to provide a solution to the above stated problems. The objective has been achieved by providing an aqueous dispersion of nano- or microcapsules as defined in claim 1.

It is another embodiment of the invention to provide a production method of the above-mentioned dispersion of nano- or microcapsules as defined in claim 9 or 10.

Other features, elements, steps, characteristics and advantages of the present invention will become more apparent from the following detailed description of preferred embodiments of the present invention. Specific embodiments of the invention are also defined in the dependent claims.

DESCRIPTION OF EMBODIMENTS

According to a first aspect of the present invention, an aqueous dispersion of nano- or microcapsules is provided, said capsules have a polymeric shell surrounding a core, the polymeric shell comprise a resin having at least one repeating unit of formula (I), (II), and/or (III),

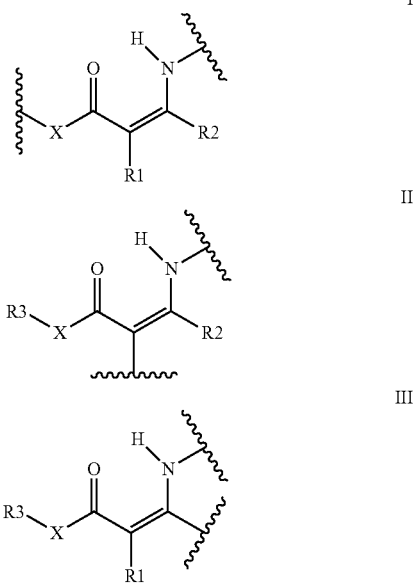

wherein R1 is selected from the group consisting of a hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group, COR4 and CNR2 is selected from the group consisting of a hydrogen, a substituted or unsubstituted alkyl group, a substituted or unsubstituted alkenyl group, a substituted or unsubstituted aralkyl group, a substituted or unsubstituted alkaryl group, a substituted or unsubstituted alkynyl group, a substituted or unsubstituted aryl or heteroaryl group and COR4

$R_1$ and $R_2$ may represent the necessary atoms to form a five to eight membered ring R3 is selected from the group consisting of a substituted or unsubstituted alkyl group, a substituted or unsubstituted alkenyl group, a substituted or unsubstituted alkynyl group, a substituted or unsubstituted aralkyl group, a substituted or unsubstituted alkaryl group and a substituted or unsubstituted aryl or heteroaryl group R4 is selected from the group consisting of a hydrogen, a substituted or unsubstituted alkyl group, a substituted or unsubstituted alkenyl group, a substituted or unsubstituted alkynyl group, a substituted or unsubstituted aryl or heteroaryl group, a substituted or unsubstituted aralkyl group, a substituted or unsubstituted alkaryl group, OR5 and NR6R7

R5 is selected from the group consisting of a substituted or unsubstituted alkyl group, a substituted or unsubstituted alkenyl group, a substituted or unsubstituted alkynyl group, a substituted or unsubstituted aralkyl group, a substituted or unsubstituted alkaryl group and a substituted or unsubstituted aryl or heteroaryl group R6 and R7 are independently selected from the group consisting of a hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group and a substituted or unsubstituted aryl or heteroaryl group R6 and R7 may represent the necessary atoms to form a five to eight membered ring X is selected from the group consisting of O, NR8 and CR9R10

R8, R9 and R10 are independently selected from the group consisting of a hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group and a substituted or unsubstituted aryl or heteroaryl group R8 and R3 may represent the necessary atoms to form a five to eight membered ring any of R3, R9 and R10 may represent the necessary atoms to form a five to eight membered ring, and which is obtainable by contacting in a liquid comprising water, an oligomeric or polymeric compound A comprising at least 2 functional groups selected from the group of functional groups —X—C(=O)—CHR1-C(=O)—R2, —X—C(=O)—C≡C—R2; or —X—C(=O)—CR1=CR2-NR11R12, the functional groups are linked by means of a linking group comprising a polyester, polyether, polyolefin, polydimethylsiloxane or polycarbonate chain, with a compound B comprising at least two —NH$_2$, —NH$_3^+$ or —N=C=O wherein R11 and R12 are independently selected from the group consisting of a hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group and a substituted or unsubstituted aryl or heteroaryl group.

In some preferred embodiments, the resin composition of the particles is made of vinylogous-urethane, vinylogous-amide, vinylogous-urea units or a combination thereof. Vinylogous urethanes are compounds containing the chemical functionality —N—C=C—C(=O)—O—. Vinylogous urea are compounds containing the chemical functionality —N—C=C—C(=O)—NR—. Vinylogous amide are compounds containing the chemical functionality —N—C=C—C(=O)—CRR'—.

In a preferred embodiment, the resin particle according to the present invention comprises at least one moiety according to formula I. In a further preferred embodiment, X represents O. In a further preferred embodiment R1 is selected from the group consisting of a hydrogen, a substituted or unsubstituted alkyl group and a substituted or unsubstituted aryl group, a hydrogen being particularly preferred. In another preferred embodiment, R2 is selected from the group consisting of a substituted or unsubstituted alkyl group and a substituted or unsubstituted aryl group. In the most preferred embodiment R2 represents a C1 to C6 alkyl group, a methyl group being the most preferred.

A. Preparation of the Aqueous Dispersion

A.1. Liquid

The aqueous dispersion can be obtained by reacting at least 2 compounds in a liquid which comprises water. Preferably the liquid is a mixture of water and an organic solvent which is not soluble in water. Non-solubility in water is defined as any water solvent combination forming a two phase system at 20° C. when mixed in a one over one volume ratio. In a particularly preferred embodiment, the water insoluble solvent has a boiling point below 100° C. at normal pressure. Esters are particularly preferred as water immiscible solvent. Suitable examples are ethyl acetate, propyl acetate, isopropyl acetate, methyl acetate, propyl formate, butyl formate, isopropyl formate, isopropyl acetate and ethyl acetate being more preferred, ethyl acetate being the most preferred.

A.2. Compound A

Compound A comprises at least 2 functional groups selected from the group of functional groups of formula —X—C(=O)—CHR1-C(=O)—R2, —C(=O)—C≡C—R2; or —C(=O)—CR1=CR2-NR4R5 and NR11R12, the at least 2 functional groups are linked by a linking group selected from the group of polyester, polyether, polyolefin, polydimethylsiloxane or polycarbonate chains.

The linking is achieved by using in the synthesis of compound A, a polyester polyol, a polycarbonate polyol, a polyether polyol, a polyacrylate polyol, an aliphatic polyester polyol, a polyolefin polyol or a mixture thereof. The introduction of these 'polymeric chains' will improve the flexibility of the resin of the wall of the capsule and hence improve adhesion to substrates and/or increase the permeability of the wall.

Examples of polycarbonate polyols are e.g. Oxymer C112, Oxymer M112 (available via Perstorp), Kuraray polyol C-2050, C-2090, C-1090 (available from Kuraray), Converge HMA-1 and Converge HMA-1 (available from Novomer Inc.), Duranol T6002, T6001, T5652, T5651, T5650J, T4672, T4671, T4692 and T4691 (available from Asahi kasei).

Very suitable polyester polyols are the ones containing terephthalic ester units and isophthalic ester units in a ratio of 1:1 mol % such as Dynacoll 7150 supplied by Evonik, Marl, Germany, Vylon 220 from Toyobo, Osaka Japan and Elitel 1401 obtained from Unitika Ltd Dusseldorf Germany. Preferably diols with a Mw equal to or less than 400 are used together with the polyester polyol. These polyols can be used singly or as mixture of two or more kinds. Additional suitable aliphatic polyester polyols, are e.g. regular (semi) crystalline or amorphous grades, e.g. based on hexane diol adipates (e.g. Dynacoll 7372 from Evonik) but also polyester polyols based on natural products such as polyester polyols made by using dimer acid or dimer diols (e.g. trade name Priplast from Croda), examples are Priplast 3192 and Priplast 1838. The raw material used to prepare certain Priplast grades, i.e. dimer diols with trade name Pripol can also be used as monomer in the PU synthesis to modify the physical properties and adhesive properties of the wall of the capsules.

In a particularly preferred embodiment, said compound A comprises at least two functional group according to —X—C(=O)—CHR$_1$—C(=O)R$_2$. In a more preferred embodiment, compound A comprises two functional groups according to —X—C(=O)—CHR$_1$—C(=O)R$_2$. In a more preferred embodiment R$_1$ represents a hydrogen and R$_2$ is selected from the group consisting of a substituted or unsubstituted alkyl group and a substituted or unsubstituted aryl group, a C1 to C6 alkyl group being even more preferred.

In a more preferred embodiment, compound A, is obtainable by reacting a β-keto-ester with a polyester polyol, a polycarbonate polyol, a polyether polyol, a polyacrylate polyol, an aliphatic polyester polyol, a polyolefin polyol or a mixture thereof. A vinylogous urethane is then obtained after reaction with compound B. In another preferred embodiment, compound A is obtainable by reacting a keto amide (e.g. CAS registry number 59692-90-9, CAS registry number 1182810918, CAS registry number 56543-91-0, CAS registry number 1182810-91-8, CAS registry number 56543-91-0, CAS registry number 2156168-44-2, CAS registry number 1696690-90-0, CAS registry number 1516406-56-6) with isocyanate terminated polyesters (Desmodur E XP2715, Desmodur LU D80), polycarbonates (CASN123256-09-7), polyethers (Desmodur E15, Desmodur XP2617), polyolefine (Nisso-PB G1000 from Nippon Soda) and mixtures thereof. A vinylogous urea is then obtained after reaction with compound B.

In another preferred embodiment, compound A is obtainable by reacting a acetoacetate ester (e.g. CAS registry number 33736-01-5, CAS registry number 168677-53-0, CAS registry number 75428-80-7, CAS Registry number 851401-63-3) with isocyanate terminated polyesters (Desmodur E XP2715, Desmodur LU D80), polycarbonates (CASN123256-09-7), polyethers (Desmodur E15, Desmodur XP2617), polyolefine (Nisso-PB G1000 from Nippon Soda) and mixtures thereof. A vinylogous urethane is then obtained after reaction with compound B.

A.3. Compound B

Preferably, compound B is an amine compound and can be selected from the group comprising diamines, triamines and polyamines. In some embodiment, compound B can be an amine such as those used as isocyanate precursor, such as diamines of the formula $R(-NH_2)_x$, wherein R is a functional linking group, preferably comprising 2 to 20 carbon atoms, selected from aliphatic, cycloaliphatic, aromatic and hetero aromatic groups.

Diamines are particularly preferred as compound B. In a particularly preferred embodiment, said compound B is represented by formula IV

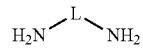

Formula IV wherein L is selected from the group consisting of a substituted or unsubstituted alkylene group, a substituted or unsubstituted alkenylene group, a substituted or unsubstituted alkynylene group, a substituted or unsubstituted alkarylene group, a substituted or unsubstituted aralkylene group and a substituted or unsubstituted arylene group, a substituted or unsubstituted alkylene group being particularly preferred.

Compound B may be chosen, for example, from aliphatic amines such as tris(2-aminoethyl)amine, ethylenediamine, tetramethylenediamine, pentamethylenediamine, hexamethylenediamine, diethylenetriamine, triethylenetetramine, tetraethylenepentamine, dihexylenetriamine, cadaverine, putrescine, hexanediamine, spermine, isophorone diamine, dimerised fatty diamine (such as are available commercially under the trade name "Priamine" from Croda International and the trade name "Versamine" from Cognis Corporation) and also aromatic and benzylic amines such as m-xylylenediamine; phenylenediamine, diaminodiphenylmethane, diaminodiphenyl sulfone and methylenebischlorodiethylaniline. Non-limiting examples include m-xylylene diamine; p-xylylenediamine; 1,3-Cyclohexanebis(methylamine), mixture of isomers; 1,2-Diaminocyclohexane; 1,5-Diamino-2-methylpentane; 4,9-Dioxa-1,12-dodecanediamine; Dytek® EP diamine; 2,2-Dimethyl-1,3-propanediamine; 2,2'-(Ethylenedioxy)bis(ethylamine); Tris(2-aminoethyl)amine; 4,4'-Methylenebis(cyclohexylamine); 4,7,10-Trioxa-1,13-tridecanediamine; all jeffamines (commercially available from Huntsman). Non-limiting examples of suitable compound B are shown in Table 1.

TABLE 1

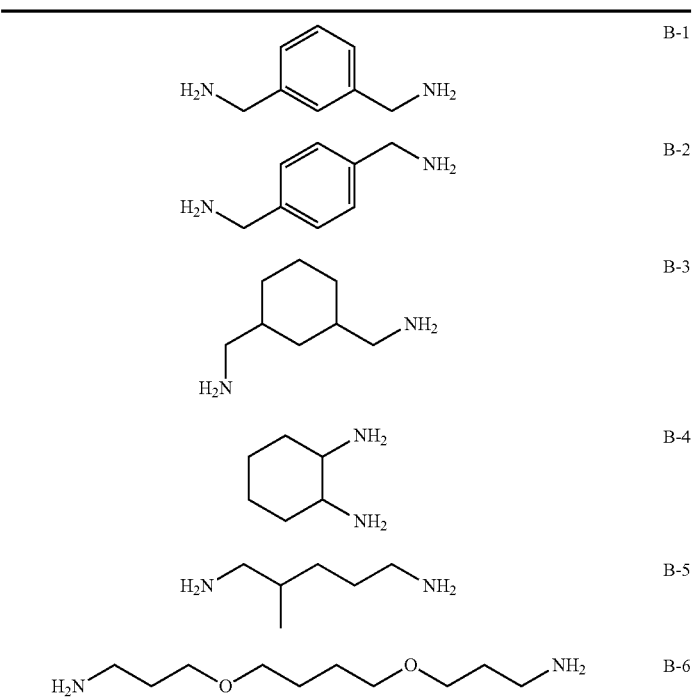

TABLE 1-continued

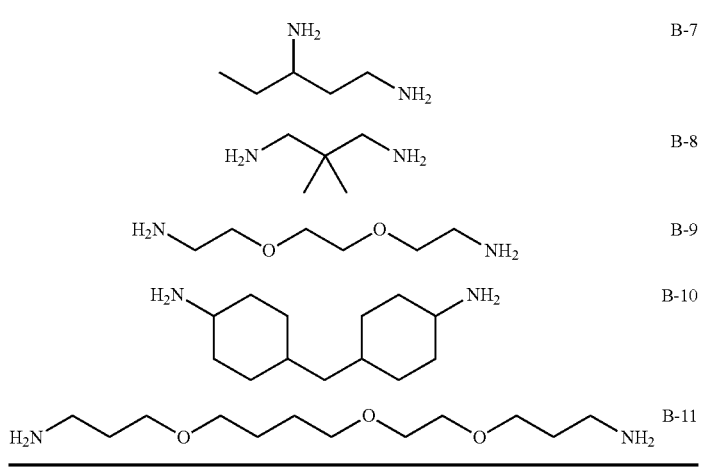

In a preferred embodiment of the invention, compound B can also be a bis amino terminated polymer or oligomer, e.g. bis amino terminated polydimethylsiloxane, other examples are: Wacker Fluid NH15D, Wacker Fluid NH40D, Wacker Fluid NH02D, Poly(ethylene glycol), α,ω-bis(amino)-terminated (CAS Number 24991-53-5). Other suitable compound B can be Jeffamines (available from Huntsman), amino terminated PTMG (Curative P-1000 from Gantrade Corporation (CAS registry number 54667-32-5) lysinol and polyethyleneimine.

A.4. Reaction of Compound A with Compound B

In one embodiment of the invention, compound A can react with compound B by bringing both compounds in an organic solvent together. The choice of the organic solvent is determined by the solubility of compound A and B. Preferably the organic solvent is selected from the group of ketones such as acetone and methyl ethyl ketone, ethers such as tetrahydrofuran and dioxolane and dioxane, acetates such as ethyl acetate and butyl acetate, nitriles such as acetonitrile, and amides such as dimethyl formamide, N-methylpyrrolidone and N-ethylpyrrolidone. These may be used singly or in combinations of two or more. Once the reaction between compound A and B is complete, hence the amount of one of the 2 compounds is substantially zero, the reaction mixture comprising the formed resin is brought into a liquid comprising water where the resin is becoming a particle. The organic solvent is then removed by evaporation, pervaporation, membrane techniques or distillation.

In a preferred embodiment of the invention, the aqueous dispersion is formed according to the invention via interfacial polymerization. This technique is well-known and has recently been reviewed by Zhang Y. and Rochefort D. (Journal of Microencapsulation, 29(7), 636-649 (2012) and by Salitin (in Encapsulation Nanotechnologies, Vikas Mittal (ed.), chapter 5, 137-173 (Scrivener Publishing LLC (2013)). In interfacial polymerization, such as interfacial polycondensation, the compound A and compound B meet at the interface of emulsion droplets and react rapidly with each other. Interfacial polymerisation requires a liquid comprising the dispersion of an oleophilic phase in an aqueous continuous phase or vice versa. Each of the phases contains at least one dissolved compound A that is capable of reacting with compound B dissolved in the other phase. Upon polymerisation, the resin having a moiety of formula (I), (II), and/or (III) is formed that is insoluble in both the aqueous and the oleophilic phase and forms capsules which shell grows upon further polymerisation.

The formed capsules according to the present invention are preferably prepared from an oleophilic dispersion in an aqueous continuous phase, the oleophilic phase preferably comprising compound A, the aqueous continuous phase comprising compound B. The oleophilic phase is in a particularly preferred embodiment, the non-water soluble organic solvent and is removed by solvent stripping before or after the particle formation.

Esters are particularly preferred as water immiscible solvent, for example ethyl acetate is particularly useful.

The dispersing of an oleophilic phase in an aqueous continuous phase can be performed by any known method in art, but is preferably performed by means of high shear equipment such as an Ultraturax T25 (Ika). The dispersed phase can be stabilised by emulsifying agents such as hydrophilic polymers such as polyvinyl alcohol, polyethylene oxides and derivatives, such as poloxamers, commercially available as Pluronics from BASF or Synperonics from Croda, starch and starch-derivatives, sugars and non-reducing sugars such as sorbitol. Additionally the use of surfactants, both anionic, cationic or non-ionic can be used to stabilise the dispersion. Examples include the agents but are not limited to described in § B.2 and more specifically disclosed in MC CUTCHEON. Functional Materials, North American Edition. Glen Rock, N.J.: Manufacturing Confectioner Publishing Co., 1990. p. 110-129.

The method for preparing a dispersion of capsules according to the invention preferably includes the following steps:
a) preparing a non-aqueous solution of compound A or B in a non-water soluble organic solvent; and
b) preparing an aqueous solution of compound B or A; and
c) dispersing the non-aqueous solution under high shear in the aqueous solution; and
d) optionally stripping the organic solvent from the mixture of the aqueous solution and the non-aqueous solution.

In a preferred embodiment, compound A or compound B can be emulsified in a liquid comprising water as a first step. The compound to be emulsified should be liquid at the reaction temperature. The droplets of compound A or B are preferably stabilised in the liquid comprising water. After the emulsion formation of compound A or B, the compound B or A is solved in the liquid comprising water so as to begin the reaction between compound A and B forming the resin having a moiety of formula (I), (II), and/or (III). Then the organic solvent may be omitted.

Regardless of the method of preparation of the capsules of the invention, the capsules are preferably stabilised by means of dispersing agents such as surfactants and polymeric dispersants. Suitable dispersing agents and polymeric dispersants are disclosed in § B.2.

In a preferred embodiment, active material can be added to the dispersed phase. As this material do not participate in the formation of the resin having a moiety of formula (I), (II), and/or (Ill), a capsule is formed having a core shell structure, the core comprising the active material. The shell comprises the resin having a moiety of formula (I), (II), and/or (III), the core comprising the active material added in the dispersed phase and which did not participate in the formation of the resin. The active material added in the dispersed phase can be selected from the group of compounds such as colorants, chemical reactants which are able to react upon application of heat and/or light, flame retardants, binders, fragrances, light stabilizers, conductive particles and polymers, magnetic particles, flavour or malodour counteraction agents, a drug, herbicides and pesticides.

Preferable colorants as active material in the core, are dyes such as disperse dyes, reactive dyes, leuco dyes, acid dyes. Suitable pigments are given in § B.2. More preferably, leuco dyes can be encapsulated by means of capsules according to the invention. Suitable colour forming compounds are: The dyes G-(18) to G-(36) disclosed by U.S. Pat. No. 6,100,009 (FUJI), the colourless dye-precursor is the leuco dye-precursor (CASRN104434-37-9) shown in EP 174054 A (POLAROID), The leuco dye precursors G-(1) to G-(17) disclosed by U.S. Pat. No. 6,100,009 (FUJI), H-donor-precursor including a carbonate group, e.g. a tBOC group, as part of its chemical structure, with preferred carbonate groups as given on page 8 of EP 605149 A (JUJO PAPER), compound HOP (CASRN 129104-70-7) is given on page 31 of EP 605149 A (JUJO PAPER) for the compound (19),H-donor-RG compounds including 4-hydroxy-4'-allyloxydiphenylsulfone and 4,4'-diallyloxy diphenylsulfone whereof the synthesis is disclosed by EP 1452334 A (RICOH), more preferably a combination is of 4,4'-Bis (tert butoxycarbonyloxy)diphenylsulfone (CASRN 1291 04-70-7) as the H-donor-FG compound with the leuco dye crystal violet lactone (CASRN 1552-42-7).

The chemical reactant as active material in the core, which may be able to react upon application of heat, is typical a cross-linker which is activated directly by heat or activated indirectly using an optothermal converting agent. In the latter, for example an infrared absorbing dye converts the infrared light of an infrared laser or infrared LEDs into heat. Examples of thermally reactive chemistry are disclosed in WO2015/158649 [0058-0066]. Most preferred thermally reactive chemistry include blocked isocyanates and more preferred examples of these blocked isocyanates are disclosed in the unpublished application EP3351603A.

The reactive chemistry in the core may also be responsive to light, such as UV light. UV curable reactive chemistry contains one or more chemical reactants, such as a monomer, oligomer or polymer, which are curable by free radical polymerization or by cationic polymerization. In a preferred embodiment, the monomer, oligomer or polymer includes at least one acrylate group as polymerisable group. Preferred compounds which can be used in the core of the particles of the invention are disclosed in WO2015/158649 [0068-0109].

The composition can be prepared in the presence of a catalyst, or an anticatalyst, or without any catalyst. The speed of stress-relaxation of the polymeric network can be therefore controlled by increasing or decreasing the speed of exchange reaction. Acid can increase the speed of the exchange reaction and base can slow down the exchange reaction.

In an embodiment, acids can be selected from acetic acid, trifluoracetic acid, etc. . . . ; and bases can be selected from DBU, dibutylamine etc. . . . . Organometallic catalyst can be used. In these embodiments, the catalyst can comprises an element selected from the group comprising tin, iron, lead, bismuth, mercury, titanium, hafnium, zirconium, and combinations thereof. In certain embodiments, the catalyst comprises a tin catalyst. Suitable tin catalysts, for purposes of the present invention, may be selected from tin(II) salts of organic carboxylic acids, e.g. tin(II) acetate, tin(II) octoate, tin(II) ethylhexanoate and tin(II) laurate. Preferably, the composition is prepared without any catalysts.

The capsules of the obtained aqueous dispersion have a numeric average diameter of between 10 nm and 100 µm, preferably between 15 nm and 10 µm, more preferably between 20 nm and 1 µm.

The obtained aqueous dispersion has an amount of resin between 1 wt. % and 80 wt. %, preferably between 5 and 50 wt. %, more preferably between 7 wt. % and 15 wt. %.

B. Aqueous Formulations

The dispersion of the capsules according to the invention is suitable to be incorporated in aqueous formulations such as inks, ink jet inks, medicinal formulations, perfumes, herbicides, pesticides, . . . . The particles are preferably present in an inkjet ink in an amount of no more than 30 wt. %, preferably between 5 and 25 wt. % based on the total weight of the ink. Aqueous formulations may further contain following additives.

B.1. Solvent

The aqueous medium of the aqueous formulations contains water, but may preferably include one or more water-soluble organic solvents. The one or more organic solvents may be added for a variety of reasons. For example, it can be advantageous to add a small amount of an organic solvent to improve the dissolution of a compound in an inkjet ink to be prepared. Preferable water-soluble organic solvents are polyols (e.g., ethylene glycol, glycerin, 2-ethyl-2-(hydroxymethyl)-1,3-propanediol, tetraethylene glycol, triethylene glycol, tripropylene glycol, 1,2,4-butanetriol, diethylene glycol, propylene glycol, dipropylene glycol, butyleneglycol, 1,6-hexanediol, 1,2-hexanediol, 1,5-pentanediol, 1,2-pentanediol, 2,2-dimethyl-1,3-propanediol, 2-methyl-2,4-pentanediol, 3-methyl-1,5-pentanediol, 3-methyl-1,3-butanediol, and 2-methyl-1,3-propanediol), amines (e.g., ethanolamine, and 2-(dimethylamino)ethanol), monohydric alcohols (e.g., methanol, ethanol, and butanol), alkyl ethers of polyhydric alcohols (e.g., diethylene glycol monomethyl ether, diethylene glycol monobutyl ether, triethylene glycol monomethyl ether, triethylene glycol monobutyl ether, ethylene glycol monomethyl ether, ethylene glycol monobutyl ether, propylene glycol monomethyl ether, propylene glycol monobutyl ether, and dipropylene glycol monomethyl ether), 2,2'-thiodiethanol, amides (e.g., N,N-dimethylformamide), heterocycles (e.g., 2-pyrrolidone and N-methyl-2-pyrrolidone), and acetonitrile.

B.2. Colorants

The colorants which can be further included in an aqueous formulation, such as an ink jet ink can be dyes or pigments. Suitable dyes include disperse dyes, reactive dyes, leuco dyes, acid dyes.

The pigments may be black, white, cyan, magenta, yellow, red, orange, violet, blue, green, brown, mixtures thereof, and the like. A colour pigment may be chosen from those disclosed by HERBST, Willy, et al. Industrial Organic Pigments, Production, Properties, Applications. 3rd edition. Wiley-VCH, 2004. ISBN 3527305769.

Suitable pigments for use in ink jet inks together with capsules according to the invention, are disclosed in paragraphs [0128] to [0138] of WO 2008/074548. The pigment particles are dispersed in an aqueous medium using a polymeric dispersant, an ionic surfactant, but preferably a self-dispersible pigment is used. The latter prevents interaction of the polymeric dispersant with the dispersing groups of resin particles of the invention which may be included in the inkjet ink (see below), since dispersion stability of the pigment is accomplished by the same technique of electrostatic stabilization as employed for the resin particles.

A self-dispersible pigment is a pigment having on its surface covalently bonded anionic hydrophilic groups, such as salt-forming groups or the same groups used as dispersing groups for the resin particles, that allow the pigment to be dispersed in an aqueous medium without using a surfactant or a resin.

The technology for making self-dispersible pigments is well-known. For example, EP1220879 A discloses pigments having attached a) at least one steric group and b) at least one organic ionic group and at least one amphiphilic counterion, wherein the amphiphilic counterion has a charge opposite to that of the organic ionic group that are suitable for inkjet inks. Also EP906371A discloses suitable surface-modified coloured pigment having attached hydrophilic organic groups containing one or more ionic groups or ionizable groups. Suitable commercially available self-dispersible colour pigments are, for example, the CAB-O-JET™ inkjet colorants from CABOT.

Pigment particles in the aqueous formulation such as inkjet inks should be sufficiently small to permit free flow of the ink through the inkjet-printing device, especially at the ejecting nozzles. It is also desirable to use small particles for maximum colour strength and to slow down sedimentation.

The average pigment particle size is preferably between 0.050 and 1 μm, more preferably between 0.070 and 0.300 μm and particularly preferably between 0.080 and 0.200 μm. Most preferably, the numeric average pigment particle size is no larger than 0.150 μm. The average particle size of pigment particles is determined with a Brookhaven Instruments Particle Sizer BI90plus based upon the principle of dynamic light scattering. The ink is diluted with demi water to a pigment concentration of 0.002 wt %. The measurement settings of the BI90plus are: 5 runs at 23° C., angle of 90°, wavelength of 635 nm and graphics=correction function.

However, for white pigment inkjet inks, the numeric average particle diameter of the white pigment is from about 50 to about 950 nm, more preferably from about 75 to about 750 nm, and still more preferably from about 100 to about 500 nm.

Suitable white pigments are given by Table 2 in [0116] of WO 2008/074548. The white pigment is preferably a pigment with a refractive index greater than 1.60. The white pigments may be employed singly or in combination. Preferably titanium dioxide is used as pigment with a refractive index greater than 1.60. Suitable titanium dioxide pigments are those disclosed in [0117] and in [0118] of WO 2008/074548. Also special colorants may be used, such as fluorescent pigments for special effects in clothing, and metallic pigments for printing a luxury look of silver and gold colours on textiles.

Suitable polymeric dispersants for the pigments are copolymers of two monomers but they may contain three, four, five or even more monomers. The properties of polymeric dispersants depend on both the nature of the monomers and their distribution in the polymer. Copolymeric dispersants preferably have the following polymer compositions:
  statistically polymerized monomers (e.g. monomers A and B polymerized into ABBAABAB);
    alternating polymerized monomers (e.g. monomers A and B polymerized into ABABABAB);
    gradient (tapered) polymerized monomers (e.g. monomers A and B polymerized into BAABBABBB);
    block copolymers (e.g. monomers A and B polymerized into AAAAAABBBBBB) wherein the block length of each of the blocks (2, 3, 4, 5 or even more) is important for the dispersion capability of the polymeric dispersant;
    graft copolymers (graft copolymers consist of a polymeric backbone with polymeric side chains attached to the backbone); and mixed forms of these polymers, e.g. blocky gradient copolymers.

Suitable dispersants are DISPERBYK™ dispersants available from BYK CHEMIE, JONCRYL™ dispersants available from JOHNSON POLYMERS and SOLSPERSE™ dispersants available from Lubrisol. A detailed list of non-polymeric as well as some polymeric dispersants is disclosed by MC CUTCHEON. Functional Materials, North American Edition. Glen Rock, N.J.: Manufacturing Confectioner Publishing Co., 1990. p. 110-129.

The polymeric dispersant has preferably a number average molecular weight Mn between 500 and 30000, more preferably between 1500 and 10000. The polymeric dispersant has preferably a weight average molecular weight Mw smaller than 100,000, more preferably smaller than 50,000 and most preferably smaller than 30,000.

The pigments are preferably present in the range of 0.01 to 20%, more preferably in the range of 0.05 to 10% by weight and most preferably in the range of 0.1 to 5% by weight, each based on the total weight of the inkjet ink. For white inkjet inks, the white pigment is preferably present in an amount of 3% to 40% by weight of the inkjet ink, and more preferably 5% to 35%. An amount of less than 3% by weight cannot achieve sufficient covering power.

B.3. Resin

The aqueous formulation comprising the dispersion of the capsules according to the invention, such as ink jet inks may further comprise an additional resin. The resin is often added to ink jet ink formulations to achieve a good adhesion of the pigment to the fibres of the textile fabric. The resin is a polymer and suitable resins can be acrylic based resins, a urethane-modified polyester resin or a polyethylene wax.

B.4. Additives

The aqueous formulation, such as an inkjet ink may further comprise a surfactant, a humectant, a biocide and a thickener as an additive.

Humectants are preferably incorporated in inkjet inks to prevent the clogging of nozzles. The prevention is due to its ability to slow down the evaporation rate of the solvents, especially of the water in the ink. The humectant is preferably an organic solvent having a higher boiling point than water. Suitable humectants include triacetin, N-methyl-2-pyrrolidone, glycerol, urea, thiourea, ethylene urea, alkyl urea, alkyl thiourea, dialkyl urea and dialkyl thiourea, diols, including ethanediols, propanediols, propanetriols, butanediols, pentanediols, and hexanediols; glycols, including propylene glycol, polypropylene glycol, ethylene glycol, polyethylene glycol, diethylene glycol, tetraethylene glycol, and mixtures and derivatives thereof. A preferred humectant is glycerol. The humectant is preferably added to the liquid formulation in an amount of 0.1 to 20 wt. % based on the total weight of the liquid.

Any known surfactant may be used in the aqueous formulation of the invention. Preferably a glycol surfactant and/or an acetylene alcohol surfactant can be used. The use of the acetylene glycol surfactant and/or the acetylene alcohol surfactant further reduces bleeding to improve printing quality, and also improves the drying property in printing to allow high-speed printing. The acetylene glycol surfactant and/or the acetylene alcohol surfactant is preferably one or more selected from 2,4,7,9-tetramethyl-5-decyne-4,7-diol, alkylene oxide adducts of 2,4,7,9-tetramethyl-5-decyne-4,7-diol, 2,4-dimethyl-5-decyn-4-ol, and alkylene oxide adducts of 2,4-dimethyl-5-decyn-4-ol. These are available, for example, from Air Products (GB) as Olfine (registered trademark) 104 series and E series, such as Olfine E1 010, or from Nissin Chemical Industry as Surfynol (registered trademark) 465 and Surfynol 61.

A biocide may be added to the formulation to prevent unwanted microbial growth, which may occur in the liquid. The biocide may be used either singly or in combination. Suitable biocides for the ink-jet ink of the present invention include sodium dehydroacetate, 2-phenoxyethanol, sodium benzoate, sodium pyridinethione-1-oxide, ethyl p-hydroxybenzoate and 1,2-benzisothiazolin-3-one and salts thereof.

Preferred biocides are Proxel™ GXL and Proxel™ Ultra 5 available from ARCH UK BIOCIDES and Bronidox™ available from COGNIS.

A biocide is preferably added to the aqueous medium in an amount of 0.001 to 3 wt. %, more preferably 0.01 to 1.0 wt. %, each based on the ink liquid.

The aqueous formulations may further comprise at least one thickener for viscosity regulation in the liquid. Suitable thickeners include urea or urea derivatives, hydroxyethylcellulose, carboxymethylcellulose, hydroxypropylcellulose, derived chitin, derived starch, carrageenan, pullulan, proteins, poly(styrenesulphonic acid), poly(styrene-co-maleic anhydride), poly(alkyl vinyl ether-co-maleic anhydride), polyacrylamide, partially hydrolyzed polyacrylamide, poly(acrylic acid), poly(vinyl alcohol), partially hydrolyzed poly(vinyl acetate), poly(hydroxyethyl acrylate), poly(methyl vinyl ether), polyvinylpyrrolidone, poly(2-vinylpyridine), poly(4-vinylpyridine) and poly(diallyldimethylammonium chloride).

The thickener is added preferably in an amount of 0.01 to 20 wt. %, more preferably 0.1 to 10 wt. % based on the total amount of the aqueous formulation.

C. Printing Method Using Aqueous Inkjet Inks Comprising Capsules of the Invention Printing methods using aqueous formulations, more particularly inkjet inks, comprising the dispersion of the invention include at least the steps of: a) applying the aqueous inkjet ink containing the dispersed capsules of the invention by means of an inkjet technique onto a substrate; and b) applying heat to make the resin of the dispersed capsules flow.

In a digital textile printing process of the invention, the textile fabric used can be made of one type of fibre or blended fibre of two or more selected from the group consisting of cotton, hemp, rayon fibre, acetate fibre, silk, nylon fibre, and polyester fibre. The fabric may be in any form, for example, a woven, knitted, or nonwoven form of the above-mentioned fibres.

In a first step of the digital textile printing method, a pre-treatment liquid containing a flocculant may be preferably applied to the fabric by spraying, coating, or pad printing. Alternatively, the pre-treatment liquid may also be applied to fabric using an ink jet head or valve jet head. These last means of applying the pre-treatment liquid have the advantage that the amount of required pre-treatment liquid is substantially lower than with the other application methods. By means of an ink jet head, it is possible to apply the pre-treatment liquid onto areas of the fabric where the image should be printed.

In a preferred embodiment of the invention, the pre-treatment liquid may comprise the dispersion according to the invention. When the pre-treatment agent is applied to fabric with an ink jet head, the particle diameter is preferably in the range 50 nm to 1 µm when determined by light scattering. A particle diameter larger than 1 µm tends to cause a deterioration in stability of jetting from the ink jet head. The particle diameter is more preferably 500 nm or less. Suitable ink jet head types for applying the pre-treatment liquid are piezoelectric type, continuous type, thermal print head type or valve jet type. Preferable capsules are the one with a core comprising a thermally reactive crosslinker and stabilised with dispersants comprising cationic dispersing groups.

Fabric to which a pre-treatment liquid has been applied may be dried before applying a coloured image. After drying, the pre-treated textile may optionally undergo a heat treatment, before the subsequent ink jetting step with ink. The heat treatment is preferably at 110 to 200° C., more preferably 130 to 160° C. Heating at 110° C. or higher enables the flow of the resin of the particle according to the invention or enables a thermally reactive crosslinker in the core of the particle to be fixed to the fibres of the fabric. Examples of the heating process include, but are not limited to, heat press, atmospheric steaming, high-pressure steaming and THERMOFIX. Any heat source can be used for the heating process; for example, an infrared ray lamp can be employed.

After the application of the pre-treatment liquid of the textile fabric, the aqueous inkjet ink according to the invention is jetted onto the substrate. Preferably the inkjet ink may comprise a colorant, more preferably a pigment. The colorant may be present in the core of the capsule and/or in the aqueous medium of the ink.

After the ink jetting step, the printed fabric is dried and heated. The drying step can be performed at the air, but the heating step must be performed by using heat sources; examples include equipment for forced-air heating, radiation heating such as IR-radiation, including NIR- and CIR radiation, conduction heating, high-frequency drying, and microwave drying. The drying step of the fabric is carried at a temperature preferably below 150° C., more preferably below 100° C., most preferably below 80° C. The heating step is preferably at 110 to 200° C., more preferably 130 to 160° C.

Another embodiment of the inkjet printing method according to the present invention includes at least the steps of: a) jetting an inkjet ink comprising a colorant and the dispersion containing resin particles with a core comprising blocked isocyanates onto a substrate; and b) applying heat to make the resin of the particles flow and to further activate the blocked isocyanates in the core of the particle. Suitable substrates are textile fabrics, leather, glass, ceramic, metallic, glass, wood, paper or polymeric surfaces. The substrate may also be primed, e.g. by a white ink.

The substrate may be porous, as e.g. textile, paper and card board substrates, or substantially non-absorbing substrates such as e.g. a plastic substrate having a polyethylene terephtalate surface.

Preferred substrates including surfaces of polyethylene, polypropylene, polycarbonate, polyvinyl chloride, polyesters like polyethylene terephthalate (PET), polyethylene naphthalate (PEN), (co)polyesters based on cyclohexyldimethanol (CHDM) (PETG), (co)polyesters based on 2,5-furandicarboxylic acid (FDCA) (PEF), copolyesters based on isosorbide (e.g. as available from Roquette and SK Chemical) and polylactic acid (PLA) and polyimide.

The substrate may also be a paper substrate, such as plain paper or resin coated paper, e.g. polyethylene or polypropylene coated paper. There is no real limitation on the type of paper and it includes newsprint paper, magazine paper, office paper, wallpaper but also paper of higher grammage, usually referred to as boards, such as white lined chipboard, corrugated board and packaging board.

The substrates may be transparent, translucent or opaque. Preferred opaque substrates includes so-called synthetic paper, like the Synaps™ grades from Agfa-Gevaert which are an opaque polyethylene terephthalate sheet having a density of 1.10 g/cm$^3$ or more.

A preferred ink jet head for the inkjet printing system is a piezoelectric ink jet head. Piezoelectric inkjet jetting is based on the movement of a piezoelectric ceramic transducer when a voltage is applied thereto. The application of a voltage changes the shape of the piezoelectric ceramic transducer in the print head creating a void, which is then filled with ink. When the voltage is again removed, the ceramic expands to its original shape, ejecting a drop of ink from the ink jet head. However the jetting of the ink according to the present invention is not restricted to piezoelectric inkjet printing. Other inkjet print heads can be used and include various types, such as a continuous type, a thermal print head type and a valve jet type.

If an optothermal converting agent is present in the core of the particles of the invention, the heating mains may be a suitable light source. If the optothermal converting agent consists of one or more infrared dyes, an infrared light source is used. Any infrared light source may be used, as long as at least part of the emitted light is suitable for generation of heat. The infrared curing means may include an infrared laser, an infrared laser diode, infrared LEDs or a combination thereof.

EXAMPLES

1. Materials

All materials used in the following examples were readily available from standard sources such as Sigma-Aldrich (Belgium) and Acros (Belgium) unless otherwise specified. The water used was demineralised water.

Acetone is acetone p.a. supplied by VWR International

Wincon Red is a leuco dye supplied by Connect Chemicals

Takenate D-131N is an isocyanate supplied by Mitsui

Cab-O-Jet 450C is a commercial cyan pigment dispersion supplied by Cabot Corporation (15% pigment)

tert-butyl acetoacetate available from Eastman

DMPA is dimethylol propionic acid supplied by Perstorp AB

Triethylamine is triethylamine supplied by Acros

PVA-sol is a 20 w % solution of Mowiol 4 88 in water, containing 0.01 w % of 1,2-benzisothiazolin-3-one potassium salt as biocide.

DYNACOLL 7150, a polyester from Evonik Industries, consisting of terephthalic acid, isophthalic acid, ethyleneglycol and neopentylglycol Synthesis of Compound Cyclohexane Bis-Acetoacetate (CDM-AA)

For the synthesis of cyclohexane dimethanol-bis-acetoacetate (0.2 mol) 30 g. (0.208 mol) of 4-(hydroxymethyl) cyclohexyl]methanol and 67.5 g of tert-butyl acetoacetate were mixed in a round-bottom flask in 40 ml of xylene. The mixture was heated in an oil-bath at 135° C. for 2 h, under stirring, while distillation of tert-butanol was performed. After cooling the xylene was removed under reduced pressure (rotavopor, 80° C., 60 mbar). The addition of 60 ml isopropanol made the cyclohexane dimethanol bis-acetoacetate (CDM-AA) precipitate. Filtration was performed to isolate the product.

Synthesis of Compound A-1: Synthesis of Polyester Bis-Acetoacetate

DYNACOLL 7150 was end-group functionalized with β-keto esters in the following manner. 50 g of DYNACOLL 7150 (0.0187 mol, 1 eq) was mixed with 29.6 g (0.187 mol, 10 eq) of tert-butyl acetoacetate. The mixture was heated till 150° C. in a round-bottom flask. After 2 hours of distillation of the t-butanol at 82° C., the mixture was cooled down to room temperature. 100 ml of acetone was added, and this solution was precipitated in 2 liter of methanol. Decantation of the precipitate was performed. This product was dissolved in 200 ml of acetone, which was then removed on a rotavapor. The solid end product was a yield of 78% (DYNA-AA).

Example 1

Synthesis of the Capsule Dispersion According to the Invention (CAPS-A)

A solution of 1.33 g Wincon Red, 2.95 g DYNA-AA and 6.5 g CDM-AA in 45 g ethyl acetate was prepared. The solution was added to a solution of 12.5 g PVA-sol, 1.49 g m-xylylene diamine and 1.065 g N,N-bis(2-aminoethyl)-1, 2-ethanediamine in 74.17 g water while stirring for five minutes with an Ultra-Turrax for 5 minutes at 5000 rpm. The ethyl acetate and part of the water was removed under reduced pressure. The weight of the mixture was adjusted with water to 100 g. The dispersion was further stored at room temperature.

The capsules were inspected under an optical microscope (leica DMRM). The capsules were found to have an average diameter of 1-2 μm.

Synthesis of a Comparative Capsule Dispersion (CAPS-B)

A solution of 1 g Wincon Red and 10.8 g Takenate D-131N in 33 g ethyl acetate was prepared. The solution was added to a solution of 12.5 g PVA-sol in 77.3 g water while stirring for 5 minutes using an Ultra Turrax at 5000 rpm. The ethyl acetate and part of the water was removed under reduced pressure. 1 g of tetraethylene pentamine was added and the weight of the mixture was adjusted with water to 100 g. The mixture was stirred for an additional 16 hours at room temperature.

The capsules were inspected under an optical microscope (leica DMRM). The capsules were found to have an average diameter of 1-2 μm.

Encapsulation Ability

To evaluate the ability of encapsulation of the capsules CAPS-A and CAPS-B, 0.2 g of the CAPS-A or CAPS-B dispersion was mixed with 0.4 g of zinksalicilate dispersion and 0.6 g of water. The aqueous formulation containing the CAPS-A was colourless, the aqueous formulation containing the CAPS-B showed a light magenta colour. The light magenta colour indicates that the leuco dye was not completely encapsulated with the comparative capsules CAPS-B. This proves that the encapsulation ability of the capsules according to the invention is higher than the encapsulation ability of the comparative polyurethane capsules.

The invention claimed is:

1. An aqueous dispersion of capsules having a polymeric shell surrounding a core, wherein the core comprises an active material and the shell comprises a resin comprising at least one repeating unit of formula I, II and/or III

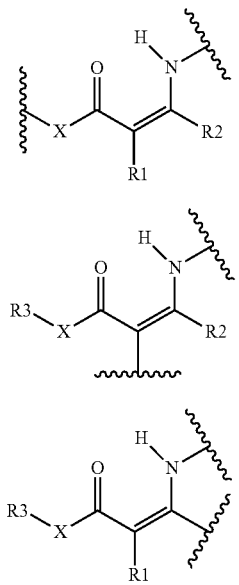

wherein
R1 is selected from the group consisting of hydrogen, a substituted or unsubstituted alkyl group, a substituted or unsubstituted alkenyl group, a substituted or unsubstituted alkynyl group, a substituted or unsubstituted aryl or heteroaryl group, a substituted or unsubstituted aralkyl group, a substituted or unsubstituted alkaryl group, C=OR4, and CN;
R2 is selected from the group consisting of hydrogen, a substituted or unsubstituted alkyl group, a substituted or unsubstituted alkenyl group, a substituted or unsubstituted alkynyl group, a substituted or unsubstituted aryl or unsubstituted aryl or heteroaryl group, a substituted or unsubstituted aralkyl group, a substituted or unsubstituted alkaryl group, and C=OR4;
optionally, R1 and R2 represent the necessary atoms to form a five to eight membered ring;
R3 is selected from the group consisting of a substituted or unsubstituted alkyl group, a substituted or unsubstituted alkenyl group, a substituted or unsubstituted alkynyl group, a substituted or unsubstituted aralkyl group, a substituted or unsubstituted alkaryl group, and a substituted or unsubstituted aryl or heteroaryl group;
R4 is selected from the group consisting of hydrogen, a substituted or unsubstituted alkyl group, a substituted or unsubstituted alkenyl group, a substituted or unsubstituted alkynyl group, a substituted or unsubstituted aryl or heteroaryl group, a substituted or unsubstituted aralkyl group, a substituted or unsubstituted alkaryl group, OR5, and NR6R7;
R5 is selected from the group consisting of a substituted or unsubstituted alkyl group, a substituted or unsubstituted alkenyl group, a substituted or unsubstituted alkynyl group, a substituted or unsubstituted aralkyl group, a substituted or unsubstituted alkaryl group, and a substituted or unsubstituted aryl or heteroaryl group;
R6 and R7 are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, and a substituted or unsubstituted aryl or heteroaryl group;
optionally, R6 and R7 represent the necessary atoms to form a five to eight membered ring;
X is selected from the group consisting of O, NR8, and CR9R10;
R8, R9, and R10 are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, and a substituted or unsubstituted aryl or heteroaryl group;
optionally, R8 and R3 represent the necessary atoms to form a five to eight membered ring;
optionally, any of R3, R9 and R10 represent the necessary atoms to form a five to eight membered ring;
and which is obtained by contacting in a liquid comprising water, a compound A comprising at least two functional groups selected from the group consisting of functional groups —X—C(=O)—CHR1-C(=O)—R2, —X—C(=O)—C≡C—R2; and —X—C(=O)—CR1=CR2-NR11R12, wherein the functional groups are linked by means of a linking group comprising a polyester, polyether, polyolefin, polydimethylsiloxane or polycarbonate chain, with a compound B comprising at least two functional groups selected from the group consisting of —$NH_2$, —$NH_3^+$ and —N=C=O;
wherein R11 and R12 are independently selected from the group consisting of hydrogen, a substituted or unsubstituted alkyl group, a substituted or unsubstituted alkenyl group, a substituted or unsubstituted alkynyl group, and a substituted or unsubstituted aryl or heteroaryl group.

2. The aqueous dispersion according to claim 1 wherein the repeating unit is of formula I and compound A comprises at least two functional groups according to the formula —X—C(=O)—CHR1-C(=O)R2, wherein X represents O.

3. The aqueous dispersion according to claim 1, wherein the repeating unit is of formula I and wherein compound B comprises at least two amine groups and further comprises an oligomer.

4. The aqueous dispersion according to claim 1 wherein the core comprises an active material selected from the group consisting of colorants, chemical reactants which are able to react upon application of heat and/or light, flame retardants, binders, fragrances, light stabilizers, conductive particles and polymers, magnetic particles, flavour or malodour counteraction agents, drugs, herbicides, pesticides, and combinations thereof.

5. The aqueous dispersion according to claim 4 wherein the core comprises a chemical reactant that is a blocked isocyanate.

6. The aqueous dispersion according to claim 4 wherein the core comprises a colorant that is a leuco dye.

7. The aqueous dispersion according to claim 4 wherein the core comprises a colorant that is a pigment.

8. An ink jet ink comprising water, a pigment, and the capsules as defined in claim 1 in an amount of 30 wt. % or less, with respect to the total weight of the ink.

9. An ink jet ink comprising water, a pigment, and the capsules as defined in claim 3 in an amount of 30 wt. % or less, with respect to the total weight of the ink.

10. An ink jet ink comprising water, a pigment, and the capsules as defined in claim 7 in an amount of 30 wt. % or less, with respect to the total weight of the ink.

11. A method of producing an aqueous dispersion as defined in claim 1 comprising:
   a) preparing a non-aqueous solution of compound A or B and an active material in a non-water soluble organic solvent;
   b) preparing an aqueous solution of compound B or A;
   c) dispersing the non-aqueous solution under high shear in the aqueous solution; and
   d) allowing a reaction between compound A and B.

12. The method of producing an aqueous dispersion according to claim 11 wherein the active material is selected from the group consisting of colorants, chemical reactants which are able to react upon application of heat and/or light, flame retardants, binders, fragrances, light stabilizers, conductive particles and polymers, magnetic particles, flavour or malodour counteraction agents, drugs, herbicides, pesticides, and combinations thereof.

13. A method of producing an aqueous dispersion as defined in claim 1 comprising:
   a) preparing a non-aqueous solution of compound A or B in a non-water soluble organic solvent;
   b) preparing an aqueous solution of compound B or A and an active material;
   c) dispersing the non-aqueous solution under high shear in the aqueous solution; and
   d) allowing a reaction between compound A and B.

14. The method of producing an aqueous dispersion according to claim 13 wherein the active material is selected from the group consisting of colorants, chemical reactants which are able to react upon application of heat and/or light, flame retardants, binders, fragrances, light stabilizers, conductive particles and polymers, magnetic particles, flavour or malodour counteraction agents, drugs, herbicides, pesticides, and combinations thereof.

15. An inkjet recording method, comprising:
   a) applying an aqueous inkjet ink as defined in claim 8 by means of an inkjet technique onto a substrate to form an image; and
   b) applying heat to the jetted image to make the resin of the capsules flow.

16. The aqueous dispersion according to claim 2, wherein the repeating unit is of formula I and wherein compound B comprises at least two amine groups and further comprises an oligomer.

* * * * *